United States Patent
Michels

(10) Patent No.: US 10,365,291 B2
(45) Date of Patent: Jul. 30, 2019

(54) METHOD FOR TRANSFERRING A LIQUID VOLUME IN AN ANALYZER

(71) Applicant: Siemens Healthcare Diagnostics Products GmbH, Marburg (DE)

(72) Inventor: Thorsten Michels, Gross-Gerau (DE)

(73) Assignee: Siemens Healthcare Diagnostics Products GmbH, Marburg (DE)

( * ) Notice: Subject to any disclaimer, the term of this patent is extended or adjusted under 35 U.S.C. 154(b) by 447 days.

(21) Appl. No.: 15/350,008

(22) Filed: Nov. 11, 2016

(65) Prior Publication Data

US 2017/0146559 A1    May 25, 2017

(30) Foreign Application Priority Data

Nov. 25, 2015  (EP) ..................................... 15196224

(51) Int. Cl.
*G01N 35/00* (2006.01)
*G01N 35/10* (2006.01)

(52) U.S. Cl.
CPC ..... *G01N 35/1011* (2013.01); *G01N 35/0099* (2013.01); *G01N 35/00722* (2013.01); *G01N 35/1016* (2013.01); *G01N 2035/00277* (2013.01)

(58) Field of Classification Search
None
See application file for complete search history.

(56) References Cited

U.S. PATENT DOCUMENTS

| | | | | | |
|---|---|---|---|---|---|
| 3,683,977 | A | * | 8/1972 | Crowe | G01N 1/18 141/130 |
| 3,855,867 | A | * | 12/1974 | Roach | B01L 3/0224 422/925 |
| 4,347,750 | A | * | 9/1982 | Tersteeg | G01N 35/00029 141/130 |
| 4,586,546 | A | * | 5/1986 | Mezei | G01N 35/1011 141/2 |
| 4,656,007 | A | * | 4/1987 | Douchy | G01N 35/1016 221/113 |
| 5,314,825 | A | * | 5/1994 | Weyrauch | G01N 35/00663 356/246 |
| 5,525,298 | A | * | 6/1996 | Anami | G01N 35/1079 422/533 |
| 5,629,201 | A | * | 5/1997 | Nugteren | C12M 23/10 422/504 |
| 5,906,795 | A | * | 5/1999 | Nakashima | B01L 3/0275 422/509 |

(Continued)

FOREIGN PATENT DOCUMENTS

EP     0670483 A2    9/1995
EP     0742435 A1    11/1996

(Continued)

OTHER PUBLICATIONS

European Search Report of European Application No. 15196224.8-1553 dated Jun. 1, 2016.

*Primary Examiner* — Jill A Warden
*Assistant Examiner* — Brittany I Fisher
(74) *Attorney, Agent, or Firm* — Dugan & Dugan, PC

(57) ABSTRACT

The present invention is in the field of automated analyzers and relates to a method for transferring a liquid volume in an analyzer. This involves the tip of a pipetting needle touching a wall of a tilted reaction vessel during the dispensing of liquid.

14 Claims, 2 Drawing Sheets

(56) References Cited

U.S. PATENT DOCUMENTS

| | | | | |
|---|---|---|---|---|
| 5,927,351 | A * | 7/1999 | Zhu | G21F 5/018 |
| | | | | 141/329 |
| 6,866,820 | B1 * | 3/2005 | Otto | B65D 47/00 |
| | | | | 215/235 |
| 7,374,720 | B2 * | 5/2008 | Toi | G01N 35/1011 |
| | | | | 222/267 |
| 7,814,805 | B2 * | 10/2010 | Angus | B01L 3/0279 |
| | | | | 422/64 |
| 2002/0110493 | A1 * | 8/2002 | Dales | B01F 7/167 |
| | | | | 422/534 |
| 2004/0018119 | A1 * | 1/2004 | Massaro | B01L 3/0217 |
| | | | | 422/509 |
| 2006/0254370 | A1 | 11/2006 | Wicky | |
| 2008/0060719 | A1 * | 3/2008 | Massaro | G01N 35/0099 |
| | | | | 141/237 |
| 2009/0007703 | A1 * | 1/2009 | Angus | B01L 3/0279 |
| | | | | 73/864.14 |
| 2010/0288060 | A1 * | 11/2010 | Ronsick | G01N 35/0099 |
| | | | | 73/864.63 |
| 2011/0086432 | A1 | 4/2011 | Herz et al. | |
| 2014/0106386 | A1 * | 4/2014 | Umeno | G01N 35/0099 |
| | | | | 435/23 |
| 2015/0127157 | A1 * | 5/2015 | Matsukuma | B25J 9/1682 |
| | | | | 700/258 |
| 2016/0238620 | A1 | 8/2016 | Shimamori et al. | |

FOREIGN PATENT DOCUMENTS

| | | |
|---|---|---|
| EP | 2308588 A2 | 4/2011 |
| FR | 2855612 A1 | 12/2004 |
| JP | 2003/302411 A | 10/2003 |
| WO | WO 2015/079829 A1 | 6/2015 |

* cited by examiner

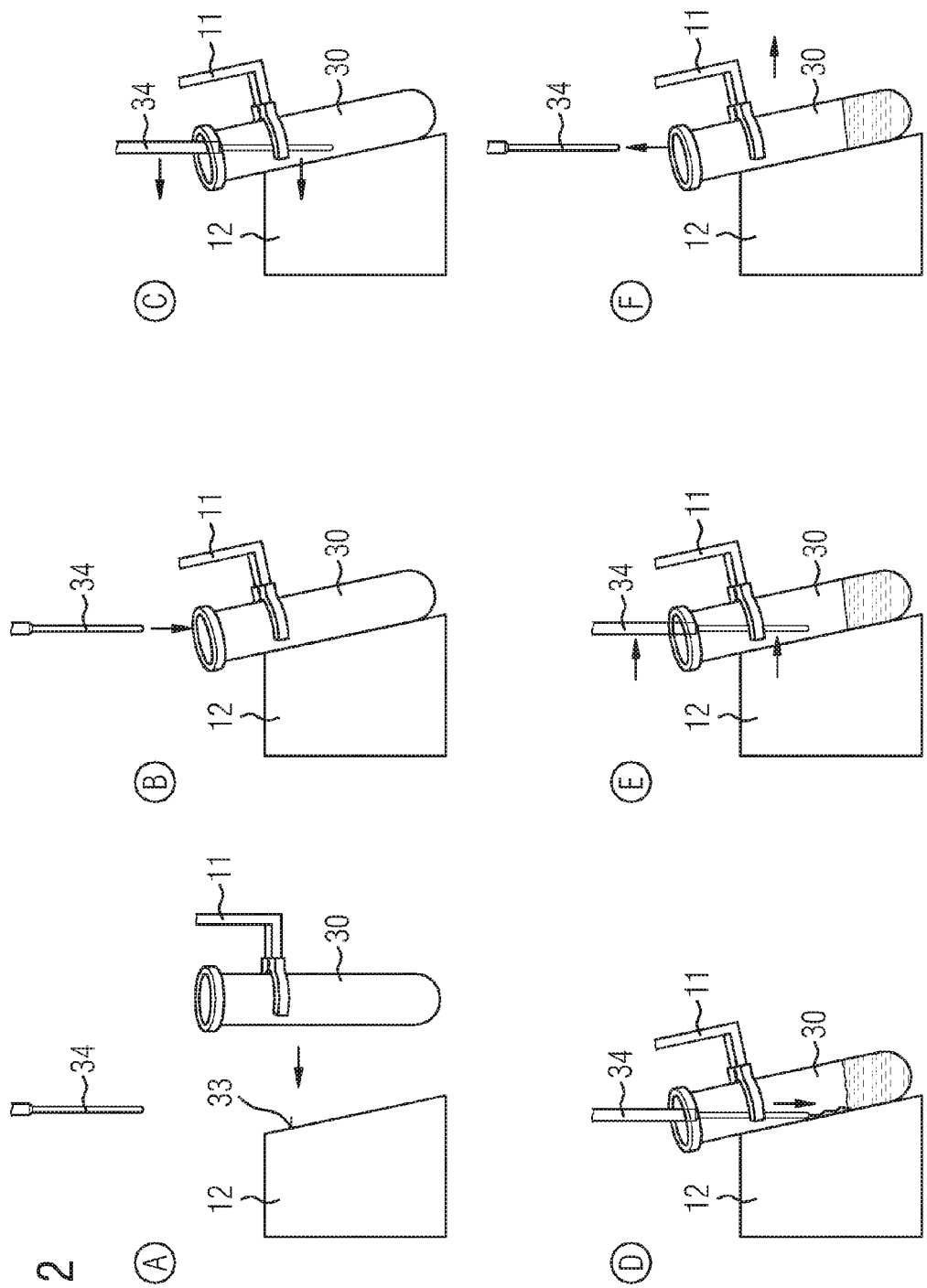

METHOD FOR TRANSFERRING A LIQUID VOLUME IN AN ANALYZER

CROSS REFERENCE TO RELATED APPLICATION

This claims priority to European Patent Application No. EP 15196224.8, filed Nov. 25, 2015, which is hereby incorporated by reference herein in its entirety for all purposes.

FIELD

The present invention is in the field of automated analyzers and relates to a method for transferring a liquid volume in an analyzer.

BACKGROUND

Current analyzers, as used routinely in chemical analysis, in forensics, in microbiology and in clinical diagnostics, are capable of carrying out a multiplicity of detection reactions and analyses with a multiplicity of samples. To be able to carry out a multiplicity of tests in an automated manner, there is a need for various automatically functioning devices for the spatial transfer of measurement cells, reaction vessels and reagent liquid containers, such as, for example, transfer arms with gripper function, transport belts or rotatable transport wheels, and also devices for the transfer of liquids, such as, for example, pipetting devices. The instruments comprise a central control unit which, by means of corresponding software, is capable of planning and working through the work steps for the desired analyses in a largely autonomous manner.

Many of the analytical methods used in such automatically functioning analyzers are based on optical techniques. Especially widespread are measurement systems based on photometric (e.g., turbidimetric, nephelometric, fluorometric or luminometric) or radiometric measurement principles. These methods allow the qualitative and quantitative detection of analytes in liquid samples without the need to provide additional separation steps. The determination of clinically relevant parameters, such as, for example, the concentration or the activity of an analyte, is done in many cases by simultaneously or successively mixing an aliquot of a body fluid from a patient with one or more test reagents in a reaction vessel, initiating a biochemical reaction which brings about a measurable change in an optical property of the test volume.

The measurement result is forwarded in turn by the measurement system to a storage unit and evaluated. Thereafter, the analyzer delivers sample-specific measurement values to a user via an output medium, such as, for example, a monitor, a printer or a network connection.

The transfer of sample liquids or of reagent liquids is typically achieved using automated pipetting devices. Such pipetting devices generally comprise a pipetting needle which is arranged perpendicularly on a shiftable transfer arm and is adjustable in height and which is connected to a pump unit, and so it is possible by means of the pipetting needle to remove a desired volume of a liquid from a container and to dispense it at another location into a target container. Typically, the pipetting needle is shifted by means of the transfer arm to a position above a liquid container and then lowered into the liquid container and the liquid present therein. After removal of the desired volume, the pipetting needle is driven upward and then, by means of the horizontally shiftable transfer arm, driven to the desired target position above a liquid container, for example above a reaction vessel or a measurement cell. There, the pipetting needle is again lowered, and the quantity of liquid is dispensed.

It is known that pipetting inaccuracies may arise as a result of portions of a liquid volume dispensed by a pipetting needle continuing to adhere on the pipetting needle tip owing to adhesion forces. This can have severe consequences especially when pipetting volumes in the microliter range, if this yields an incorrect composition of a reaction volume and generates faulty measurement results.

To avoid such pipetting inaccuracies, attempts are typically made to pipette the liquid volume onto the vessel inner wall, so that an adhesion of the liquid on the pipetting needle tip is avoided.

In the prior art, pipetting needles having slightly curved tips are used to this end, for example. However, this has the disadvantage of limited usefulness, since, for example, such pipetting needles cannot be used even to pierce tube caps.

In another method for avoiding air bubbles when adding a reagent liquid to a sample liquid, the pipetting operation is controlled such that the pipetting needle is lowered into a reaction vessel in a vertical direction and in a central manner, and is then shifted in a horizontal direction, such that the tip of the pipetting needle touches the perpendicular inner wall of the reaction vessel lengthwise in a perpendicular manner, and in this position the liquid volume is then dispensed (WO-A1-2015/079829).

SUMMARY

It is thus an object of the present invention to provide means and methods which make it possible to achieve a high precision in pipetting operations in an automated analyzer.

The object is substantially achieved by the vessel into which a liquid volume is to be dispensed by means of a pipetting needle being held in an inclined position, and so the longitudinal axis of the vessel is tilted relative to the longitudinal axis of the pipetting needle. The pipetting needle tip is then horizontally driven to the inner wall of the vessel, the liquid is dispensed while the pipetting needle tip touches the vessel inner wall and, after the dispensing of the liquid, the pipetting needle tip is moved away from the vessel inner wall in a horizontal direction before it is vertically raised out of the vessel.

It was found that the horizontal movement of the pipetting needle tip to the tilted vessel wall and away therefrom ensures an improved adhesion of the dispensed liquid in the vessel and thereby increases the precision of the liquid transfer.

The invention thus provides a method for transferring a liquid volume in an analyzer comprising at least one pipetting device mounted on a first shiftable transfer arm and having a pipetting needle and a gripper mounted on a second shiftable transfer arm and intended for a reaction vessel. The method comprises the following steps:

a) grabbing a reaction vessel using the gripper;

b) removing a defined liquid volume from a liquid container using the pipetting device;

c) shifting the pipetting device to a position above the reaction vessel;

d) lowering the pipetting needle in a vertical direction into the reaction vessel held by the gripper, to a position in which the pipetting needle does not touch a wall of the reaction vessel;

e) shifting the pipetting device in a horizontal direction such that the tip of the pipetting needle touches the inner wall of the reaction vessel;

f) dispensing the defined liquid volume into the reaction vessel;

g) retracting the pipetting device in a horizontal direction to a position in which the pipetting needle does not touch a wall of the reaction vessel; and h) raising the pipetting needle in a vertical direction out of the reaction vessel held by the gripper.

The method is further distinguished by the fact that the reaction vessel is held in an inclined position by the gripper at least during the execution of method steps e) to g), i.e., at the time of touching of the inner wall of the reaction vessel by the pipetting needle tip, at the time of dispensing of liquid and at the time of disengaging of contact between pipetting needle tip and vessel inner wall, and so the longitudinal axis of the reaction vessel is tilted relative to the longitudinal axis of the pipetting needle.

In the inclined position, preference is given to the longitudinal axis of the reaction vessel being tilted by an angle of 5° to 20°, preferably of 9° to 15°, very particularly preferably of 12°, relative to the longitudinal axis of the pipetting needle. This range of tilt angles ensures that there is neither adhesion of liquid on the exterior of the pipetting needle tip nor droplet formation on the vessel wall, but that instead the dispensed liquid volume entirely flows downward along the vessel wall in the direction of the base of the reaction vessel.

The reaction vessel can be held in the inclined position by the gripper during further method steps as well. Alternatively, the reaction vessel is held in the inclined position by the gripper at least during the execution of method steps d) to h), i.e., said vessel is already held in said position during the lowering of the pipetting needle in a vertical direction into the reaction vessel held by the gripper and continues to be held in said position during the raising of the pipetting needle in a vertical direction out of the reaction vessel held by the gripper.

It is practical for at least method steps c) to h) to take place in the stated order. However, it is possible for method steps a) and b) or a) and c) to take place independently of one another with respect to time, i.e., at the same time, one after the other, or with temporal overlap.

The shiftable transfer arms for the spatial transfer of the various functional units, such as pipetting devices or grippers, can be designed to be linearly shiftable or else swiveling.

A pipetting needle is substantially a cylindrical hollow needle having a central hollow channel. The distal end of the pipetting needle, at which typically the outlet opening of the hollow channel is also provided, is also referred to as the tip of the pipetting needle.

A "gripper for a reaction vessel" is understood to mean a device which makes it possible to grip, hold and release a reaction vessel. Preferably, a reaction vessel is gripped, held and released by means of form-fitting pairing or force-fitting pairing using the gripper. Preference is given to mechanical grippers, which can be designed to be rigid, rigid/articulated or elastic as one-finger, two-finger or multi-finger grippers. Suitable grippers are, for example, described in EP-A2-2308588 or EP-A1-0742435.

In a preferred variant of the method, the gripper for a reaction vessel is designed to be a single piece and elastically deformable. This makes gripping via a snapping effect possible when the gripper is moved with sufficient force against a reaction vessel. Only upon overcoming of a disengagement force, which is required in order to open the gripper, is the enclosed reaction vessel released.

Reaction vessels typically used in automated analyzers are designed to be tubular and have an opening. They can have different cross-sectional shapes; for example, they can have a round, oval, triangular, rectangular or square-shaped cross-sectional shape. A "reaction vessel" in the context of the present invention is explicitly understood to also mean measurement cells and cuvettes which have defined optical properties and are therefore suitable for spectrophotometric, fluorometric, luminometric or other optical analytical techniques. The reaction vessels can consist of plastic and be intended for single use. Alternatively, the reaction vessels can also consist of glass.

The grabbing of the reaction vessel using the gripper in step a) is typically effected from a perpendicular position of the reaction vessel in an accommodation position. Automated analyzers frequently have moving incubation units which have a multiplicity of accommodation positions for the accommodation of an individual reaction vessel in each case. The perpendicular position with the opening upward is the typical position of the reaction vessels in use, since they are to accommodate or already contain liquid volumes.

In a preferred embodiment of the method according to the invention, the inclined position of the reaction vessel is brought about by the reaction vessel being pushed by means of a shifting movement of the gripper in a horizontal direction against a sloped surface. Said embodiment is especially simple to carry out without the need to take complicated measures for executing and controlling the tilting movement. The sloped surface can, for example, be formed by a component which is simple, planar, wall-shaped and tilted with respect to the vertical and which is mounted on the travel path of the gripper, for example on the base plate of the analyzer. Alternatively, a portion of a component already present in the analyzer, such as, for example, an outer wall of a wash station for pipetting needles or the foot of a stand arm, can be easily designed as a sloped surface. In any case, the slope of the surface must be selected such that the reaction vessel is guided to the desired inclined position. Said embodiment is preferably combinable with an elastically deformable gripper in which it is possible to move the reaction vessel from the perpendicular position to an inclined position when said reaction vessel is pushed with sufficient force against a sloped surface and in which it is possible to move the reaction vessel from the inclined position back to the perpendicular position when said reaction vessel is moved away from the sloped surface.

In another embodiment of the method according to the invention, the inclined position of the reaction vessel is brought about by a tipping movement of the gripper. Said embodiment is preferably combinable with a gripper comprising a controllable joint.

The inclined position of the reaction vessel is preferably effected before or during the vertical lowering of the pipetting needle into the reaction vessel held by the gripper.

After completion of the dispensing of liquid and the retraction of the pipetting device to a position in which the pipetting needle no longer touches the reaction vessel wall, the reaction vessel is brought back to the perpendicular position. This can be effected either before or even during the raising of the pipetting needle in a vertical direction out of the reaction vessel.

The present invention further provides an automated analyzer comprising at least one pipetting device mounted on a first shiftable transfer arm and having a pipetting needle, a gripper mounted on a second shiftable transfer arm and intended for a reaction vessel, a multiplicity of accommodation positions for reaction vessels, and comprising a control device configured such that it controls a method according to the invention, as described above, for transferring a liquid volume.

Preferably, the control device is configured such that it controls a method comprising the following steps:

a) grabbing a reaction vessel using the gripper;
b) removing a defined liquid volume from a liquid container using the pipetting device;
c) shifting the pipetting device to a position above the reaction vessel;
d) lowering the pipetting needle in a vertical direction into the reaction vessel held by the gripper, to a position in which the pipetting needle does not touch a wall of the reaction vessel;
e) shifting the pipetting device in a horizontal direction such that the tip of the pipetting needle touches the inner wall of the reaction vessel;
f) dispensing the defined liquid volume into the reaction vessel;
g) retracting the pipetting device in a horizontal direction to a position in which the pipetting needle does not touch a wall of the reaction vessel; and
h) raising the pipetting needle in a vertical direction out of the reaction vessel held by the gripper; and
i) tilting the reaction vessel, and so the reaction vessel is held in an inclined position by the gripper at least during the execution of method steps e) to g), and so the longitudinal axis of the reaction vessel is tilted relative to the longitudinal axis of the pipetting needle.

The tilting of the reaction vessel is preferably effected before or during the vertical lowering of the pipetting needle into the reaction vessel held by the gripper.

An analyzer according to the invention preferably comprises an element having a surface tilted with respect to the vertical, and a control system which is further configured such that the inclined position of the reaction vessel is brought about by the reaction vessel being pushed by means of a shifting movement of the gripper in a horizontal direction against the sloped surface of the element.

The element having a surface tilted with respect to the vertical can, for example, be formed by a component which is simple, planar and wall-shaped and which is mounted on the travel path of the gripper, for example on the base plate of the analyzer. Alternatively, a portion of a component already present in the analyzer, such as, for example, an outer wall of a wash station for pipetting needles or the foot of a stand arm, can be easily designed as a sloped surface. In any case, the slope of the surface must be selected such that the reaction vessel is guided to the desired inclined position. Said embodiment is preferably combinable with the use of an elastically deformable gripper, in which it is possible to move the reaction vessel from the perpendicular position to an inclined position when said reaction vessel is pushed with sufficient force against a sloped surface and in which it is possible to move the reaction vessel from the inclined position back to the perpendicular position when said reaction vessel is moved away from the sloped surface.

In another embodiment of the automated analyzer, the gripper for the reaction vessel comprises a controllable joint and the control system is further configured such that the inclined position of the reaction vessel is brought about by a tilting movement of the gripper being brought about by a movement of the joint.

BRIEF DESCRIPTION OF THE DRAWINGS

The invention will be elucidated below with the aid of a drawing, where:

FIG. 2 shows a pipetting operation according to the invention.

In all the figures, the same parts are provided with the same reference signs.

DETAILED DESCRIPTION

Figure 1:
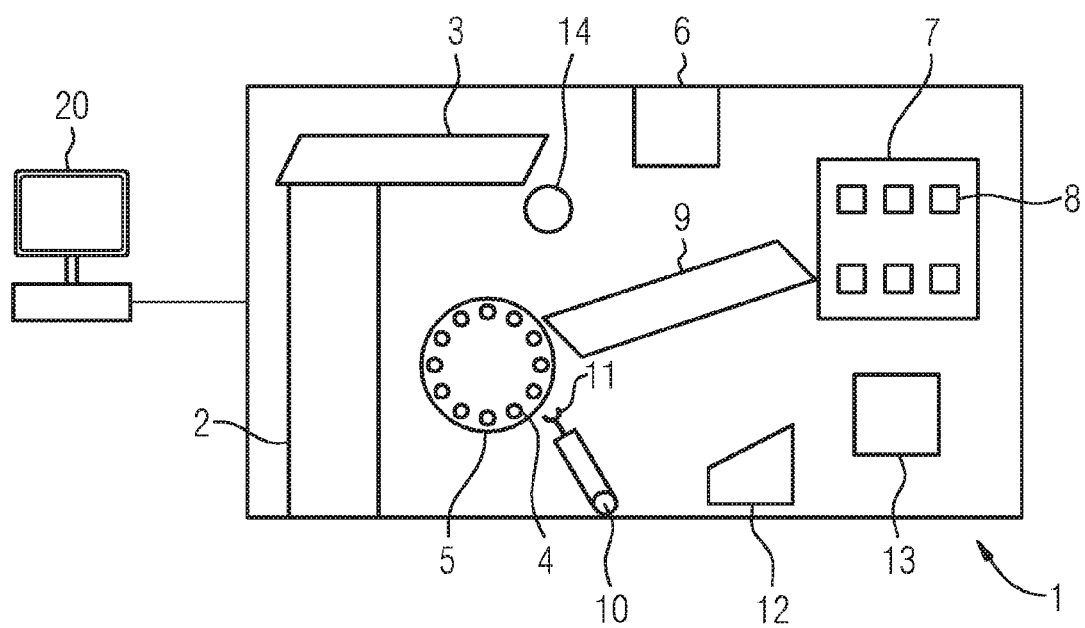
FIG. 1 shows an automated analyzer according to the invention.

FIG. 1 is a schematic representation of an automated analyzer 1 comprising some components present therein. Here, only the most important components are depicted in a greatly simplified manner in order to elucidate the fundamental function of the automated analyzer 1, without depicting in detail here the individual parts of each component.

The automated analyzer 1 is designed to carry out a very wide variety of different analyses of blood or other body fluids in a fully automated manner, without activities of a user being required for this purpose. On the contrary, required interventions by a user are limited to maintenance or repair and refill tasks when, for example, cuvettes need to be refilled or liquid containers need to be exchanged.

The patient samples are fed to the automated analyzer 1 via a feed track 2 on carriages not depicted in detail. Information concerning the analyses to be carried out for each sample can, for example, be transferred by means of barcodes which are attached to the sample vessels and which are read in the automated analyzer 1. With the aid of a first pipetting device 3, sample aliquots are removed from the sample vessels by means of a pipetting needle.

The sample aliquots are fed to cuvettes which are likewise not depicted in detail, which cuvettes are arranged in a perpendicular position in accommodation positions 4 of a rotatable incubation unit 5 adjusted to a temperature of 37° C. The cuvettes are taken from a cuvette storage container 6. Reagent vessels 8 containing various reagent liquids are kept in the reagent vessel storage container 7 cooled to about 8-10° C. In order to transfer reagent liquid into a cuvette, the cuvette is taken from the incubation unit 5 with the aid of the gripper 11, which is mounted on a swiveling transfer arm 10 and is adjustable in height, and shifted to a component 12 having a surface tilted by about 12° with respect to the vertical. Owing to pushing of the cuvette against the sloped surface of the component 12, the cuvette is guided to an inclined position. Reagent liquid is removed from a reagent vessel 8 by means of the pipetting needle of a second pipetting device 9 and dispensed into the cuvette, which already contains a sample aliquot and which is pressed against the component 12, in order to provide a reaction volume. The cuvette containing the reaction volume is transported back to the incubation unit 5 and set down by the gripper 11 in an accommodation position 4. After the incubation time, the cuvette containing the reaction volume is transported by a second, undepicted transfer arm having a gripper from the incubation unit 5 to a photometric measurement unit 13, where the absorbance of the reaction volume is measured.

A wash station 14 is provided for the cleaning of the pipetting needles of the pipetting devices 3, 9. After each pipetting operation, the pipetting devices 3, 9 are each shifted to the wash station 14; the pipetting needle is lowered and cleaned.

The entire process is controlled by a control unit 20, such as a computer connected via a data cable for example, supported by a multiplicity of further electronic circuits and microprocessors within the automated analyzer 1 and its components, which electronic circuits and microprocessors are not depicted in detail.

FIG. 2 is a schematic representation of a few steps of the method according to the invention for transferring a liquid volume in an automated analyzer, which is not depicted in detail. Part A shows a cuvette 30 which is held by a gripper 11 and which is moved toward a component 12 having a surface 33 tilted by 12° with respect to the vertical as a result of a movement of the transfer arm, which is not depicted in detail and on which the gripper 11 is mounted, in the direction of the arrow, i.e., in a horizontal manner. A pipetting needle 34, by means of which a volume of a reagent liquid has already been removed from a reagent vessel, is already situated in a position above the opening of the cuvette 30. The cuvette 30 is moved in the direction of the component 12 having the sloped surface 33 until it is pushed against the sloped surface 33. This is shown in part B. Only when the cuvette 30 is brought into an inclined position is the pipetting needle 34 lowered in a vertical direction into the cuvette 30 held by the gripper 11. As shown in part C, the vertical movement of the pipetting needle 34 ends in a position in which the pipetting needle 34 does not touch a wall of the cuvette 30. Thereafter, the pipetting needle 34 is shifted in a horizontal direction until the tip of the pipetting needle 34 touches the inner wall of the cuvette 30. As shown in part D, the reagent liquid is dispensed by the pipetting device into the cuvette 30 only in this position, i.e., when the pipetting needle tip touches the vessel wall. Only after the entire liquid volume to be transferred has been dispensed is, as shown in part E, the pipetting needle 34 retracted in a horizontal direction to a position in which the pipetting needle 34 no longer touches a wall of the cuvette 30. Lastly, the pipetting needle 34 is moved in a vertical direction out of the cuvette 30 held by the gripper 11, as shown in part F, and the cuvette 30 can be transported either to the incubation unit or directly to a measurement unit.

LIST OF REFERENCE SIGNS

1 Analyzer
2 Feed track
3 Pipetting device
4 Accommodation position
5 Incubation unit
6 Cuvette storage container
7 Reagent vessel storage container
8 Reagent vessel
9 Pipetting device
10 Transfer arm
11 Gripper
12 Component having a sloped surface
13 Measurement unit
14 Wash station
20 Control unit
30 Cuvette
33 Sloped surface
34 Pipetting needle

What is claimed is:

1. A method for transferring a liquid volume in an analyzer, the analyzer comprising a pipetting device mounted on a first shiftable transfer arm and having a pipetting needle and a gripper mounted on a second shiftable transfer arm and configured for a reaction vessel, the method comprising:

(a) grabbing a reaction vessel using the gripper;
(b) removing a defined liquid volume from a liquid container using the pipetting device;
(c) shifting the pipetting device to a position above the reaction vessel;
(d) lowering the pipetting needle in a vertical direction into the reaction vessel held by the gripper, to a position in which the pipetting needle does not touch an inner wall of the reaction vessel;
(e) shifting the pipetting device in a horizontal direction such that a tip of the pipetting needle touches the inner wall of the reaction vessel;
(f) dispensing the defined liquid volume into the reaction vessel;
(g) retracting the pipetting device in a horizontal direction to a position in which the pipetting needle does not touch the inner wall of the reaction vessel; and
(h) raising the pipetting needle in a vertical direction out of the reaction vessel held by the gripper,
wherein the reaction vessel is held in an inclined position by the gripper at least during execution of (e) to (g), and so a longitudinal axis of the reaction vessel is tilted relative to a longitudinal axis of the pipetting needle.

2. The method as claimed in claim 1, wherein, in the inclined position, the longitudinal axis of the reaction vessel is tilted by an angle of 5° to 20° relative to the longitudinal axis of the pipetting needle.

3. The method as claimed in claim 1, wherein the reaction vessel is held in the inclined position by the gripper at least during execution of (d) to (h).

4. The method as claimed in claim 1, wherein the grabbing of the reaction vessel using the gripper in (a) is effected from a perpendicular position in an accommodation position and the inclined position of the reaction vessel is brought about by the reaction vessel being pushed by means of a shifting movement of the gripper in a horizontal direction against a sloped surface.

5. The method as claimed in claim 1, wherein the gripper is a single piece and elastically deformable.

6. The method as claimed in claim 1, wherein the grabbing of the reaction vessel using the gripper in (a) is effected from a perpendicular position in an accommodation position and the inclined position of the reaction vessel is brought about by a tilting movement of the gripper.

7. The method as claimed in claim 6, wherein the gripper comprises a controllable joint.

8. An automated analyzer comprising at least one pipetting device mounted on a first shiftable transfer arm and having a pipetting needle, a gripper mounted on a second shiftable transfer arm and configured for a reaction vessel, a multiplicity of accommodation positions for reaction vessels, and comprising a control device that controls a method comprising:

(a) grabbing a reaction vessel using the gripper;
(b) removing a defined liquid volume from a liquid container using the pipetting device;
(c) shifting the pipetting device to a position above the reaction vessel;
(d) lowering the pipetting needle in a vertical direction into the reaction vessel held by the gripper, to a position in which the pipetting needle does not touch an inner wall of the reaction vessel;
(e) shifting the pipetting device in a horizontal direction such that a tip of the pipetting needle touches the inner wall of the reaction vessel;
(f) dispensing the defined liquid volume into the reaction vessel;

(g) retracting the pipetting device in a horizontal direction to a position in which the pipetting needle does not touch the inner wall of the reaction vessel;

(h) raising the pipetting needle in a vertical direction out of the reaction vessel held by the gripper; and (i) tilting the reaction vessel, and so the reaction vessel is held in an inclined position by the gripper at least during execution of (e) to (g), and so a longitudinal axis of the reaction vessel is tilted relative to a longitudinal axis of the pipetting needle.

9. The automated analyzer as claimed in claim 8, wherein, in the inclined position, the longitudinal axis of the reaction vessel is tilted by an angle of 5° to 20° relative to the longitudinal axis of the pipetting needle.

10. The automated analyzer as claimed in claim 8, further comprising an element having a surface tilted with respect to vertical, and in which the control device is configured such that the inclined position of the reaction vessel is brought about by the reaction vessel being pushed by a shifting movement of the gripper in a horizontal direction against the sloped surface of the element.

11. The automated analyzer as claimed in claim 10, wherein the gripper is a single piece and elastically deformable.

12. The automated analyzer as claimed in claim 8, in which the gripper comprises a controllable joint and in which the control device is configured such that the inclined position of the reaction vessel is brought about by a tilting movement of the gripper being brought about by a movement of the joint.

13. The automated analyzer as claimed in claim 8, wherein, in the inclined position, the longitudinal axis of the reaction vessel is tilted by an angle of 9° to 15° relative to the longitudinal axis of the pipetting needle.

14. The method as claimed in claim 1, wherein, in the inclined position, the longitudinal axis of the reaction vessel is tilted by an angle of 9° to 15° relative to the longitudinal axis of the pipetting needle.

* * * * *